(12) United States Patent
Langdon et al.

(10) Patent No.: US 7,682,350 B2
(45) Date of Patent: Mar. 23, 2010

(54) DISPOSABLE ABSORBENT ARTICLES

(75) Inventors: Frederick Michael Langdon, Blue Ash, OH (US); Luke Robinson Magee, Cincinnati, OH (US); Gregory Ashton, Cincinnati, OH (US); Mark John Ciesko, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/250,255

(22) Filed: Oct. 14, 2005

(65) Prior Publication Data

US 2007/0088312 A1    Apr. 19, 2007

(51) Int. Cl.
*A61F 13/15* (2006.01)
(52) U.S. Cl. .................. 604/396; 604/389; 604/390; 604/387; 604/394; 604/385.27; 604/385.29; 604/386
(58) Field of Classification Search .......... 604/389, 604/390, 396, 387, 386, 394, 385.27, 385.29, 604/385.01
See application file for complete search history.

(56) References Cited

U.S. PATENT DOCUMENTS

| | | | |
|---|---|---|---|
| 3,848,594 A | 11/1974 | Buell | |
| 3,860,003 A | 1/1975 | Buell | |
| 3,911,173 A | 10/1975 | Sprague, Jr. | |
| 3,929,135 A | 12/1975 | Thompson | |
| 4,089,765 A | 5/1978 | Dudley | |
| 4,324,246 A | 4/1982 | Mullane et al. | |
| 4,342,314 A | 8/1982 | Radel et al. | |
| 4,463,045 A | 7/1984 | Ahr et al. | |
| 4,515,595 A | 5/1985 | Kievit et al. | |
| 4,573,986 A | 3/1986 | Minetola et al. | |
| 4,609,518 A | 9/1986 | Curro et al. | |
| 4,610,678 A | 9/1986 | Weisman et al. | |
| 4,617,022 A | 10/1986 | Pigneul et al. | |
| 4,629,643 A | 12/1986 | Curro et al. | |
| 4,662,875 A | 5/1987 | Hirotsu et al. | |
| 4,673,402 A | 6/1987 | Weisman et al. | |
| 4,695,278 A | 9/1987 | Lawson | |
| 4,699,622 A | 10/1987 | Toussant et al. | |
| 4,704,114 A * | 11/1987 | Wilson et al. .......... | 604/385.22 |
| 4,704,115 A | 11/1987 | Buell | |

(Continued)

FOREIGN PATENT DOCUMENTS

WO    WO 94/14395 A1    7/1994

(Continued)

*Primary Examiner*—Jacqueline F. Stephens
(74) *Attorney, Agent, or Firm*—Laura L. Whitmer; George H. Leal

(57) ABSTRACT

A disposable absorbent article has a front waist edge, a back waist edge, a topsheet, a backsheet attached to at least a portion of the topsheet, and an absorbent core disposed therebetween. A waist member is attached to a wearer-facing surface of the disposable absorbent article or between the topsheet and the backsheet adjacent to the front waist edge and the back waist edge. The waist member is unattached to an outer-facing surface of the disposable absorbent article. The waist member extends outward from the front waist edge and the back waist edge such that at least a region of the waist member is visible from a vantage point external to the disposable absorbent article, thereby providing the appearance of a finished front waist edge or the appearance of a finished back waist edge.

19 Claims, 9 Drawing Sheets

U.S. PATENT DOCUMENTS

| | | |
|---|---|---|
| 4,710,189 A | 12/1987 | Lash |
| 4,747,846 A | 5/1988 | Boland et al. |
| 4,770,656 A | 9/1988 | Proxmire et al. |
| 4,785,996 A | 11/1988 | Ziecker et al. |
| 4,795,454 A | 1/1989 | Dragoo |
| 4,808,176 A | 2/1989 | Kielpikowski |
| 4,808,178 A | 2/1989 | Aziz et al. |
| 4,834,735 A | 5/1989 | Alemany et al. |
| 4,834,736 A | 5/1989 | Boland et al. |
| 4,834,738 A | 5/1989 | Kielpikowski et al. |
| 4,836,070 A | 6/1989 | Spano et al. |
| 4,842,596 A | 6/1989 | Kielpikowski et al. |
| 4,842,666 A | 6/1989 | Werenicz |
| 4,846,815 A | 7/1989 | Scripps |
| 4,872,871 A | 10/1989 | Proxmire et al. |
| 4,888,231 A | 12/1989 | Angstadt |
| 4,892,536 A | 1/1990 | Desmarais et al. |
| 4,894,060 A | 1/1990 | Nestegard |
| 4,909,803 A | 3/1990 | Aziz et al. |
| 4,940,464 A | 7/1990 | Van Gompel et al. |
| 4,946,527 A | 8/1990 | Battrell |
| D311,251 S | 10/1990 | Jones |
| 4,963,140 A | 10/1990 | Robertson et al. |
| 4,968,312 A | 11/1990 | Khan |
| 4,990,147 A | 2/1991 | Freeland |
| D315,630 S | 3/1991 | Larsen |
| 5,006,394 A | 4/1991 | Baird |
| 5,037,416 A | 8/1991 | Allen et al. |
| 5,062,840 A | 11/1991 | Holt et al. |
| D323,920 S | 2/1992 | Pitts |
| 5,092,861 A | 3/1992 | Nomura et al. |
| D325,256 S | 4/1992 | Landsman et al. |
| 5,137,537 A | 8/1992 | Herron et al. |
| 5,147,345 A | 9/1992 | Young et al. |
| 5,151,092 A | 9/1992 | Buell et al. |
| 5,171,236 A | 12/1992 | Dreier et al. |
| D334,619 S | 4/1993 | Barraza |
| 5,221,274 A | 6/1993 | Buell et al. |
| 5,242,436 A | 9/1993 | Weil et al. |
| 5,246,433 A | 9/1993 | Hasse et al. |
| 5,260,345 A | 11/1993 | Desmarais et al. |
| 5,269,775 A | 12/1993 | Freeland et al. |
| D342,997 S | 1/1994 | Buck et al. |
| 5,306,266 A | 4/1994 | Freeland |
| 5,342,338 A | 8/1994 | Roe |
| D352,151 S | 11/1994 | Warnock |
| 5,387,207 A | 2/1995 | Dyer et al. |
| 5,397,318 A | 3/1995 | Dreier |
| 5,398,648 A | 3/1995 | Spath et al. |
| 5,499,978 A | 3/1996 | Buell et al. |
| 5,507,736 A | 4/1996 | Clear et al. |
| 5,514,121 A | 5/1996 | Roe et al. |
| 5,518,801 A | 5/1996 | Chappell et al. |
| 5,540,671 A | 7/1996 | Dreier |
| 5,545,158 A | 8/1996 | Jessup |
| 5,554,142 A | 9/1996 | Dreier et al. |
| 5,554,143 A | 9/1996 | Roe et al. |
| 5,569,234 A | 10/1996 | Buell et al. |
| 5,571,096 A | 11/1996 | Dobrin et al. |
| 5,591,152 A | 1/1997 | Buell et al. |
| 5,607,760 A | 3/1997 | Roe |
| 5,609,587 A | 3/1997 | Roe |
| 5,625,222 A | 4/1997 | Yoneda et al. |
| 5,635,191 A | 6/1997 | Roe et al. |
| 5,643,588 A | 7/1997 | Roe et al. |
| 5,653,703 A | 8/1997 | Roe et al. |
| 5,725,518 A | 3/1998 | Coates |
| D403,400 S | 12/1998 | Bernard et al. |
| D404,185 S | 1/1999 | Lanter et al. |
| 5,865,823 A | 2/1999 | Curro |
| 5,897,545 A | 4/1999 | Kline et al. |
| 5,941,864 A | 8/1999 | Roe |
| 5,957,908 A | 9/1999 | Kline et al. |
| 5,968,025 A | 10/1999 | Roe et al. |
| 5,977,430 A | 11/1999 | Roe et al. |
| 5,989,380 A | 11/1999 | Frischer |
| 5,997,520 A | 12/1999 | Ahr et al. |
| 6,013,063 A | 1/2000 | Roe et al. |
| 6,120,487 A | 9/2000 | Ashton |
| 6,120,489 A | 9/2000 | Johnson et al. |
| 6,168,584 B1 | 1/2001 | Allen et al. |
| 6,432,098 B1 | 8/2002 | Kline et al. |
| 6,491,996 B2 | 12/2002 | Digangi |
| 6,548,431 B1 | 4/2003 | Bansal et al. |
| 6,607,515 B2 | 8/2003 | Glaug et al. |
| 6,639,119 B2 | 10/2003 | Roe et al. |
| 6,680,422 B2 | 1/2004 | Roe |
| 6,716,441 B1 | 4/2004 | Osborne et al. |
| 6,743,324 B2 | 6/2004 | Hargett et al. |
| 2003/0088227 A1 | 5/2003 | Schneider et al. |
| 2003/0233082 A1 | 12/2003 | Kline et al. |
| 2004/0039362 A1 | 2/2004 | Roe et al. |
| 2004/0049168 A1 | 3/2004 | Van Gompel et al. |
| 2004/0060648 A1 | 4/2004 | Thorson et al. |
| 2004/0060649 A1 | 4/2004 | Van Gompel et al. |
| 2004/0064121 A1 | 4/2004 | Van Gompel et al. |
| 2004/0078018 A1 | 4/2004 | Van Gompel et al. |
| 2004/0116886 A1 | 6/2004 | Van Gompel et al. |
| 2004/0225273 A1 | 11/2004 | Ashton et al. |
| 2005/0009173 A1 | 1/2005 | Amand |
| 2005/0027267 A1 | 2/2005 | Van Dyke et al. |
| 2005/0125877 A1 | 6/2005 | Benjamin et al. |
| 2005/0125923 A1 | 6/2005 | Benjamin et al. |
| 2005/0129743 A1 | 6/2005 | Benjamin et al. |

FOREIGN PATENT DOCUMENTS

| | | |
|---|---|---|
| WO | WO 95/16746 A1 | 6/1995 |
| WO | WO 95/24173 A2 | 9/1995 |
| WO | WO 2004/071780 A2 | 8/2004 |

* cited by examiner

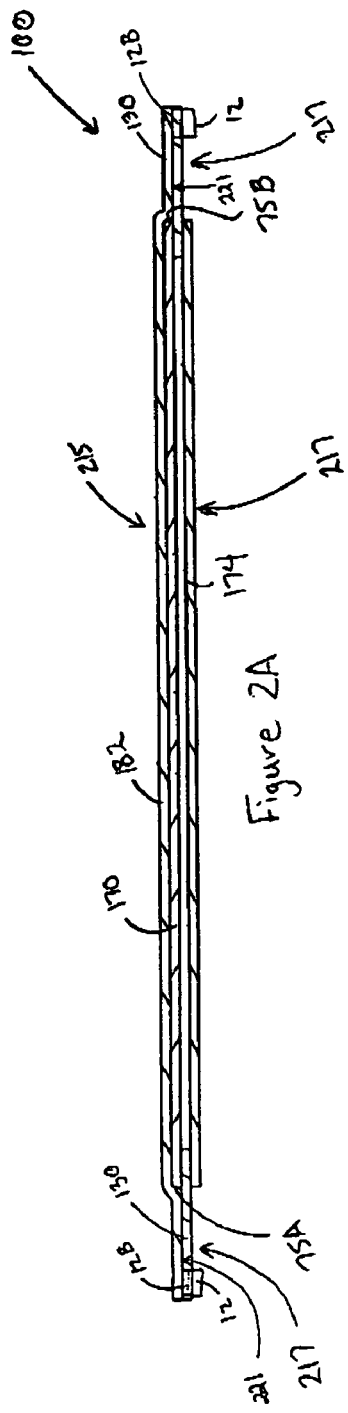
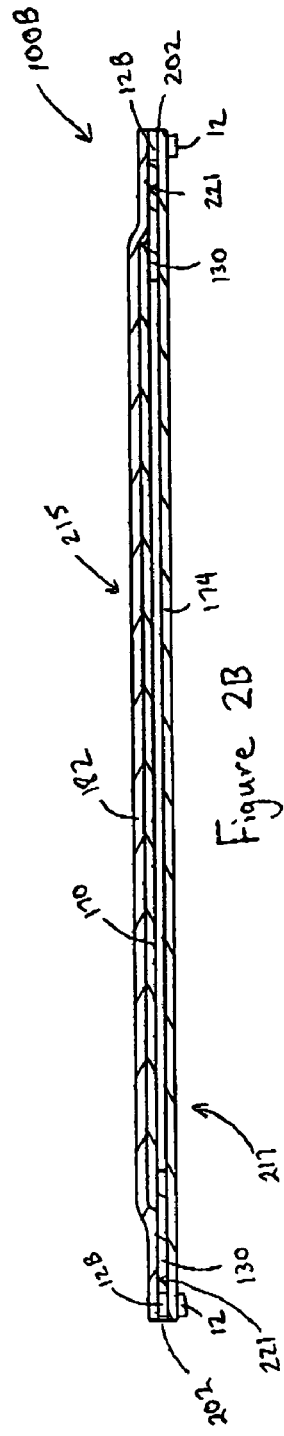
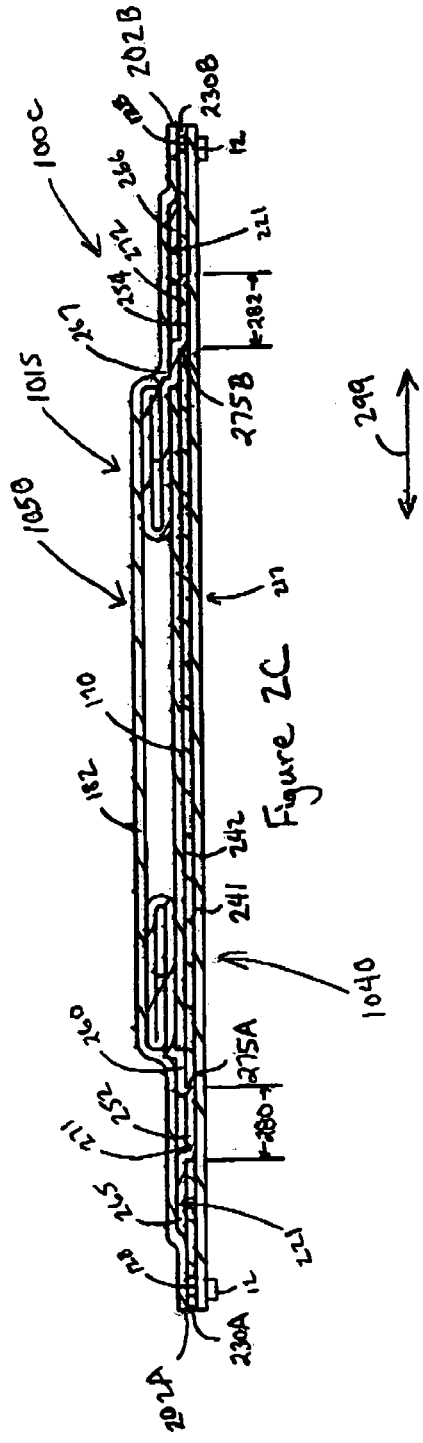
Figure 2A
Figure 2B
Figure 2C

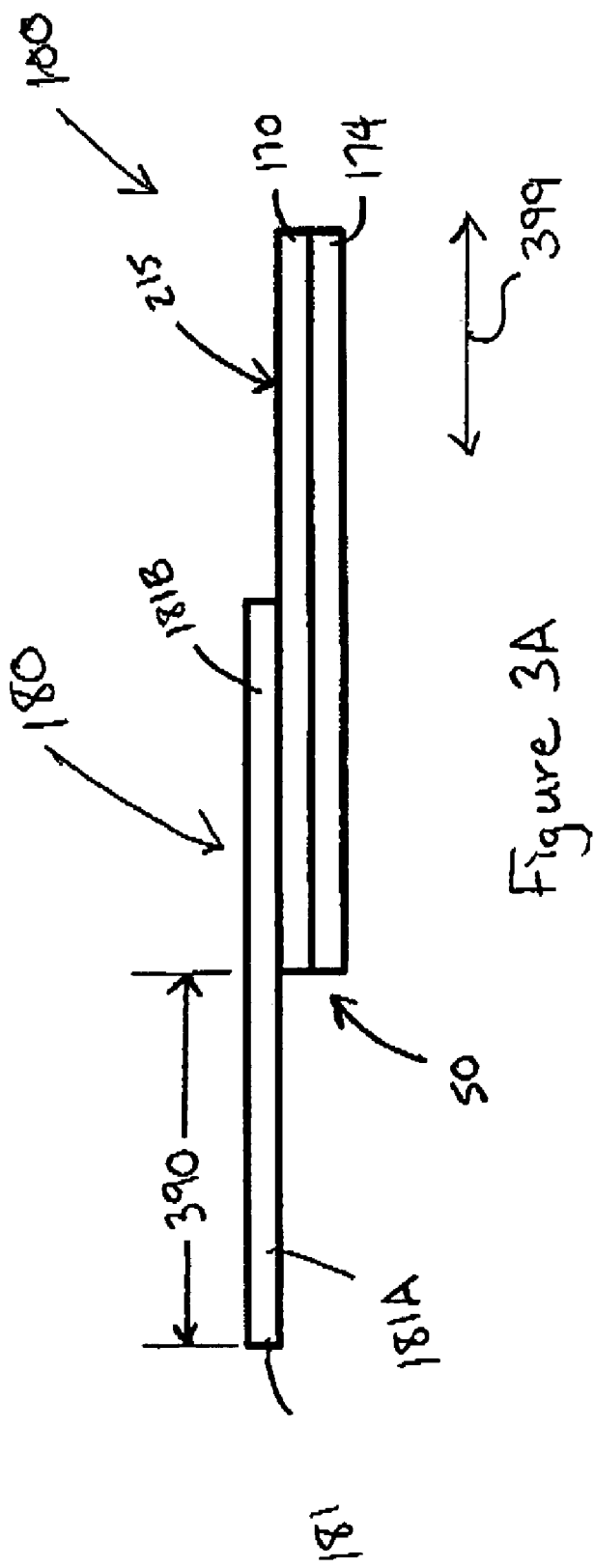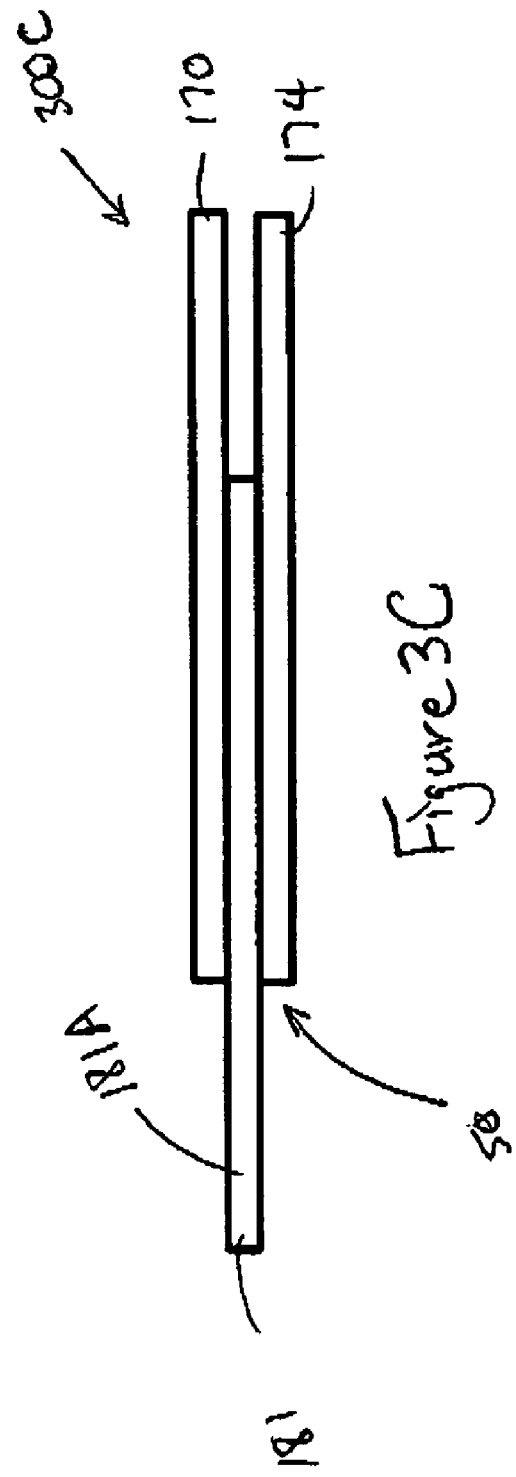
Figure 3A
Figure 3C

DISPOSABLE ABSORBENT ARTICLES

FIELD OF THE INVENTION

The invention relates to disposable absorbent articles, such as diapers, adult incontinence articles, and the like including an appearance of a finished waistband. More particularly, the present invention pertains to a disposable absorbent article providing an appearance of a finished waistband and optionally finished leg openings.

BACKGROUND OF THE INVENTION

It has long been known that absorbent articles such as conventional taped diapers, pull-on diapers, training pants, sanitary napkins, pantiliners, incontinence briefs, and the like, offer the benefit of receiving and containing urine and/or other bodily exudates. One absorbent article which has gained much popularity is the pull-on diaper, particularly for children who are able to walk and who may be engaged in toilet training.

Pull-on diapers generally include a front waist region, a back waist region, and a crotch region between the front waist region and the back waist region. The front waist region and the back waist region can be disposed adjacent to a front waist edge and a back waist edge of the pull-on diaper. Typically, the front waist region and the back waist region can be joined via pairs of side panels to form a waist opening and a pair of leg openings. Both the front waist edge and the back waist edge can make up a portion of the waist opening, and a pair of longitudinal edges can make up a substantial portion of the leg openings.

In general, pull-on diapers leave the front waist edge, the back waist edge, and the longitudinal edges unfinished. Typically, these edges include a topsheet and a backsheet. A drawback of an unfinished edge is that consumers generally associate the unfinished edge with a lower quality product.

It is known to provide edge finishing materials on a front waist edge, a back waist edge, and longitudinal edges. However, the process can be complex particularly for the application of edge finishing materials to the front waist edge or the back waist edge. For example, the edge finishing material typically is folded about the front waist edge and the back waist edge and attached to the topsheet and the backsheet in both the front waist region and the back waist region. However, folding edge finishing materials about the front waist edge and the back waist edge can increase the complexity of the process.

Consequently, a need exists for a disposable absorbent article which provides an appearance of a finished front waist edge and an appearance of a finished back waist edge and reduces the complexity of the process for providing the appearance of the finished front waist edge and/or back waist edge. Additionally, a need exists for a disposable absorbent article which provides an appearance of finished front and/or back waist edges in conjunction with an appearance of finished longitudinal edges, thereby communicating quality to the consumer.

SUMMARY OF THE INVENTION

Disposable absorbent articles constructed in accordance with the present invention can provide the appearance of finished waist edges, thereby communicating quality to the consumer. In one embodiment, a disposable absorbent article comprises a front waist region, a back waist region, a crotch region disposed between the front and back waist region, a front waist edge, and a back waist edge. The disposable absorbent article further comprises a topsheet, a backsheet attached to at least a portion of the topsheet, and an absorbent core disposed between the topsheet and the backsheet.

The disposable absorbent article further comprises a waist member attached to a wearer-facing surface of the disposable absorbent article or between the topsheet and the backsheet, adjacent to the front waist edge or adjacent to the back waist edge. Additionally, the waist member is unattached to an outer-facing surface of the disposable absorbent article. The waist member extends outward from the front waist edge or the back waist edge, such that at least a region of the waist member is visible from a vantage point external to the disposable absorbent article, thereby providing the appearance of a finished front waist edge or the appearance of a finished back waist edge.

In another embodiment, a disposable pant comprises a chassis. The chassis includes a topsheet, a backsheet attached to at least a portion of the topsheet, an absorbent core disposed between the topsheet and the backsheet; a front waist region disposed adjacent to a front waist edge, a back waist region disposed adjacent to a back waist edge, and a crotch region disposed between the front waist region and the back waist region; and a first longitudinal edge and a second longitudinal edge.

The disposable pant further comprises a pair of front side panels attached to the chassis in the front waist region. A first front side panel extends outward from the first longitudinal edge in the front waist region, and a second front side panel extends outward from the second longitudinal edge in the front waist region. The disposable pant further comprises a pair of back side panels attached to the chassis in the back waist region. A first back side panel extends outward from the first longitudinal edge in the back waist region, and a second back side panel extends outward from the second longitudinal edge in the back waist region. The pair of front side panels and the pair of back side panels are capable of attaching to each other, thereby forming a waist opening and a pair of leg openings.

The disposable pant further comprises a waist member having a first segment and a second segment. The first segment is attached to the topsheet in the front waist region and to each of the pair of front side panels, and the second segment is attached to the topsheet in the back waist region and to each of the pair of back side panels. The first segment and the second segment are attached to the topsheet on a wearer-facing surface of the disposable pant. The first segment and the second segment are attached to the disposable pant such that the waist member can encircle a waist of a wearer when the disposable pant is donned on the wearer. Additionally, the first segment extends outward from the front waist edge, and the second segment extends outward from the back waist edge, such that at least a region of the first segment and at least a region of the second segment are visible from a vantage point external to the disposable pant, thereby providing the appearance of a finished front waist edge and the appearance of a finished back waist edge.

In another embodiment, in addition to the waist member described above, a disposable pant-like article may further comprise an outer cover having a front waist region, a back waist region, and a crotch region disposed therebetween. The outer cover may further comprise a first backsheet layer which can define an outer surface of the disposable pant-like absorbent article.

The disposable pant-like absorbent article may further comprise a pair of elastically extensible front side panels and a pair of elastically extensible back side panels. Both the front side panels and the back side panels can be disposed on a wearer-facing surface of the article and attached to a portion of the first backsheet layer.

The disposable pant-like absorbent article may further comprise an absorbent assembly having a first longitudinal edge and a second longitudinal edge. The absorbent assembly may include a topsheet, a second backsheet layer associated with the topsheet, and an absorbent core disposed between said topsheet and the second backsheet layer. The second backsheet layer can be disposed on the first backsheet layer. The absorbent assembly can be attached to the wearer-facing surface of the disposable pant-like absorbent article such that the first and second longitudinal edges are in a spaced apart relationship with each of the front and back side panels, thereby defining a front longitudinally orientated non-elasticized portions and a rear longitudinally orientated non-elasticized portions therebetween.

The disposable pant-like absorbent article may further comprise a first barrier cuff and a second barrier leg cuff. The first barrier cuff can be attached to the first longitudinal edge of the absorbent assembly. The second barrier leg cuff can be attached to the second longitudinal edge of said absorbent assembly.

BRIEF DESCRIPTION OF THE DRAWINGS

FIG. 2A is an exaggerated cross sectional view showing the disposable absorbent article of FIG. 1B as seen through section line 2A-2A.

FIGS. 2B-2D are exaggerated cross sectional views showing other embodiments of disposable absorbent articles constructed in accordance with the present invention.

FIG. 3A is an exaggerated cross sectional view showing the disposable absorbent article of FIG. 1B as seen through line 3A-3A.

FIGS. 3B-3E are exaggerated cross sectional views showing other embodiments of disposable absorbent articles constructed in accordance with the present invention.

DETAILED DESCRIPTION OF THE INVENTION

Definitions

Figure 1A:
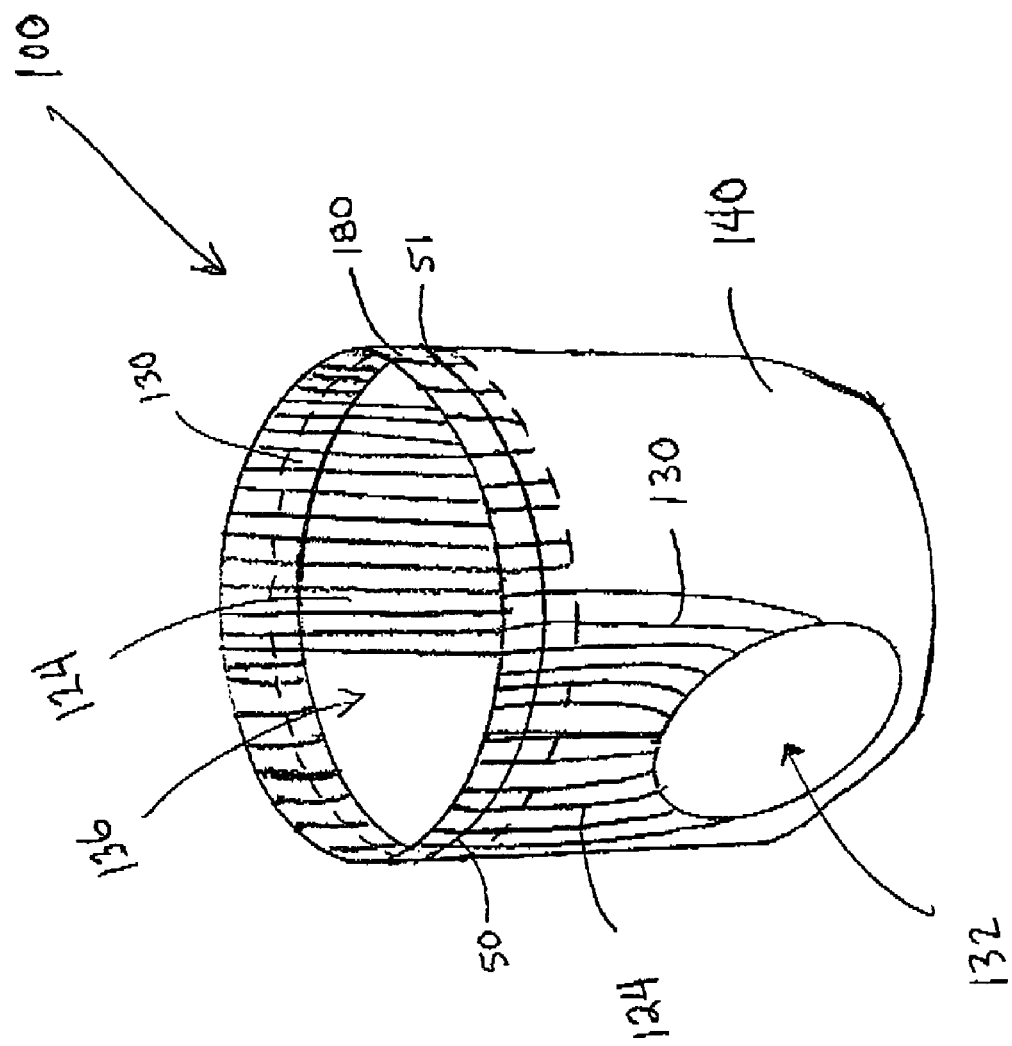
FIG. 1A shows a disposable absorbent article constructed in accordance with the present invention.

As used herein, the term "absorbent article" refers to devices that absorb and contain body exudates and, more specifically, refers to devices that are placed against or in proximity to the body of a wearer to absorb and contain the various exudates discharged from the body.

The terms "activating", "activation", "mechanical activation" or "ring rolling", refer to a process of intermeshing an element between a plurality of intermeshing teeth. This process can be utilized to render a laminated structure elastically extensible.

The term "attached" refers to elements being connected or united by fastening, adhering, bonding, etc. by any method suitable for the elements being fastened, secured, or joined, together and their constituent materials. Many suitable methods for attaching elements together are well-known, including adhesive bonding, pressure bonding, thermal bonding, mechanical fastening, etc. Such attachment methods may be used to attach elements together over a particular area either continuously or intermittently. The term "attached" includes elements which are integrally formed with another element.

The terms "corrugations" or "rugosities" are used to describe hills and valleys that occur in a substrate or in a laminated structure. Neither term, i.e. "corrugations" nor "rugosities" mandates that either the hills or valleys created are uniform in nature.

As used herein "denier" refers to a measurement of weight of a nonwoven fiber per 9,000 m of length of the nonwoven fiber. Unless otherwise noted, the measurement is denier per fiber.

As used herein, the term "diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

The term "disposable" is used herein to describe absorbent articles that generally are not intended to be laundered or otherwise restored or reused as absorbent articles (i.e., they are intended to be discarded after a single use and, preferably, to be recycled, composted or otherwise discarded in an environmentally compatible manner).

As used herein, the term "discrete edge member" or "edge member" refer to a discrete elongate member that can wrap about a portion of a longitudinal edge or extend outward from the longitudinal edge of a disposable absorbent article. Discrete edge members as described herein can provide a soft, finished appearance to portions of the longitudinal edge of a disposable absorbent article that form the leg openings of an absorbent article when the absorbent article is worn.

As used herein "elastically extensible" refers to characteristics of extensible materials that have the ability to return to approximately their original dimensions after a force that extended the extensible material is removed. Herein, any material or element described as "extensible" may also be "elastically extensible" unless otherwise provided.

The term "longitudinal" refers to a direction running from one waist edge of the article to an opposing waist edge of the article and generally parallel to a line which corresponds to the maximum linear dimension of the article. Directions within ±45° of the longitudinal direction are considered to be "longitudinal".

The term "lateral" refers to a direction running from one side edge of the article to an opposing side edge of the article and generally at a right angle to the longitudinal direction and in the same plane as the longitudinal direction. Directions within ±45° of the lateral direction are considered to be "lateral".

The terms "wearer-facing" and "outer-facing" as used herein refer to the relative location of an element or a surface of an element or group of elements. "Wearer-facing" implies the element or surface is nearer to the wearer during wear. "Outer-facing" implies the element or surface is more remote from the wearer during wear (i.e., element or surface is nearer to the wearer's garments that can be worn over the disposable absorbent article).

The terms "pant", "training pant", "closed diaper", "prefastened diaper", and "pull-on diaper", as used herein, refer to disposable garments having a waist opening and leg openings designed for infant or adult wearers. A pant can be configured such that the pant has a closed waist and leg openings prior to being donned on the wearer, or the pant can be configured such that the waist is closed and the leg openings formed while on the wearer. A pant may be preformed by any suitable technique including, but not limited to, attaching together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened, or rear waist fastened). Examples of suitable pants are disclosed in U.S. Pat. No. 5,246,433; U.S. Pat. No. 5,569,234; U.S. Pat. No. 6,120,487; U.S. Pat. No. 6,120,489; U.S. Pat. No. 4,940,464; U.S. Pat. No. 5,092,861; U.S. Pat. No. 5,897,545; U.S. Pat. No. 5,957,908; and U.S. Patent Publication No. 2003/0233082 A1.

As used herein "tactile difference" refers to a perceptible dissimilarity between a first element and a second element— the dissimilarity being at least perceptible by touch. For example, tactile difference may exist between a waist member and a portion or element of a disposable absorbent article to which the waist member is attached.

As used herein "vantage point" refers to a position which allows a view of an object(s), element(s), article(s), or any combination thereof.

As used herein, the term "waist member" refers to a discrete member that extends outward from a front waist edge and/or a back waist edge of a disposable absorbent article. "Waist members" as described herein provide a soft, finished appearance to portions of the front waist edge and/or back waist edge of the disposable absorbent article.

DESCRIPTION

A disposable absorbent article constructed in accordance with the present invention can provide an appearance of a finished front waist edge and/or an appearance of a finished back waist edge, thereby communicating quality to a consumer. Additionally, a disposable absorbent article constructed in accordance with the present invention can provide an appearance of finished longitudinal edges.

As shown in FIG. 1A, a disposable absorbent article 100 constructed in accordance with the present invention may comprise a chassis 140, front side panels 124, and back side panels 130. The front side panels 124 and the back side panels 130 can be elastically extensible. As shown, the disposable absorbent article 100 is in a pre-fastened configuration and further comprises a waist opening 136 and a pair of leg openings 132 (only one leg opening 132 is shown).

In some embodiments, the front side panels 124 in conjunction with the back side panels 130 can form a portion of the leg openings 132 when the disposable absorbent article 100 is fastened. The front side panels 124 and/or the back side panels 130 can form a portion of the leg openings 132 which would be disposed on an outer surface of a leg of a wearer. A crotch region of the disposable absorbent article 100 in conjunction with a first waist region and a second waist region can form a portion of the leg openings 132 which would be disposed on an inner surface of the leg of the wearer.

The disposable absorbent article 100 may further comprise a waist member 180. The waist member 180 can be elastically extensible and can encircle a waist of a wearer. As shown, the waist member 180 may extend outward from a front waist edge 50 and outward from a back waist edge 51 such that a region of the waist member 180 is visible from a vantage point external to the disposable absorbent article 100. Generally, the waist member 180 can be under tension prior to attaching to the chassis 140. So, upon release of at least a portion of the tension applied to the waist member 180, the waist member 180 and a portion of the chassis 140 attached thereto can corrugate. This corrugation of the chassis 140 can allow the waist member 180 and the chassis 140 to expand and contract about the waist of a wearer, thereby providing more comfort and improved fit to a wearer.

Figure 1B:
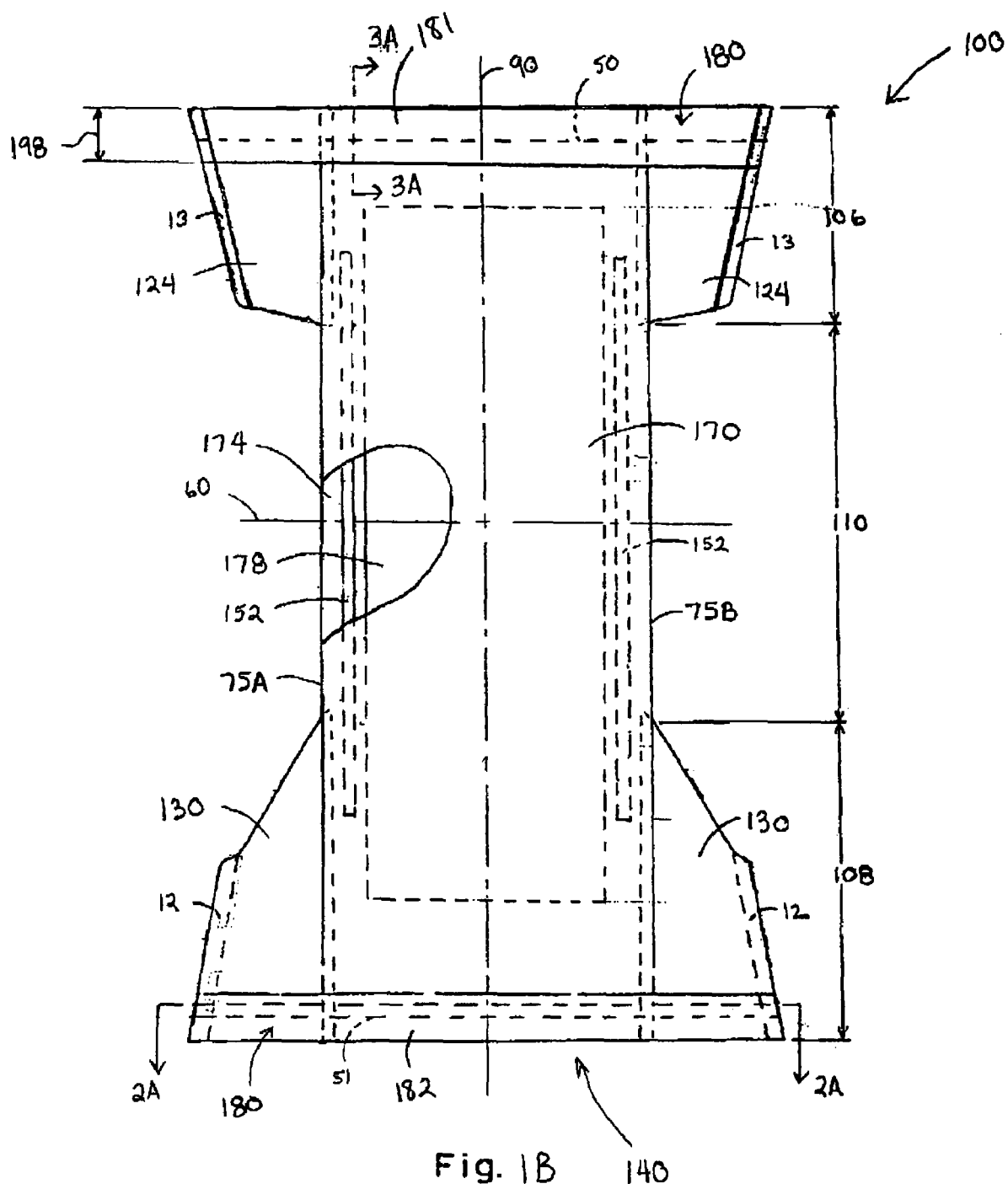
FIG. 1B is a partial cut-away view showing the disposable absorbent article of FIG. 1A in a flat, uncontracted state (i.e., without elastic induced contraction).

As shown in FIG. 1B, the portion of the disposable absorbent article 100 that faces a wearer is oriented towards the viewer. The disposable absorbent article 100 may comprise the chassis 140 which includes a front waist region 106, a back waist region 108, and a crotch region 110 disposed between the front waist region 106 and the back waist region 108. The chassis 140 may further comprise a topsheet 170, a backsheet 174, and an absorbent core 178. The absorbent core 178 can be positioned between at least a portion of the topsheet 170 and the backsheet 174.

The periphery of the chassis 140 can be defined by the longitudinal edges 75A and 75B; the front waist edge 50, and the back waist edge 51. The longitudinal edges 75A and 75B run generally parallel to a longitudinal centerline 90 of the disposable absorbent article 100. The front waist edge 50 and the back waist edge 51 run generally parallel to a lateral centerline 60 of the disposable absorbent article 100. The chassis 140 may further comprise elastic leg features 152 which can be disposed adjacent to the longitudinal edges 75A and 75B.

Front side panels 124 can extend outboard from the longitudinal edges 75A and 75B of the chassis 140 in the front waist region 106. Back side panels 130 can extend outboard from longitudinal edges 75A and 75B of the chassis 140 in the back waist region 108. The front side panels 124 can be joined to the back side panels 130 via front attachment elements 13 and back attachment elements 12 to form the waist opening 136 (see FIG. 1A) and the leg openings 132 (see FIG. 1A) of the disposable absorbent article 100.

As shown, in some embodiments, the waist member 180 may comprise a first segment 181 which can be disposed in the front waist region 106, and/or a second segment 182 which can be disposed in the back waist region 108. In some embodiments, the waist member 180 can be attached to the topsheet 170 in both the front waist region 106 and the back waist region 108. The first segment 181 and/or the second segment 182 can be disposed between the first longitudinal edge 75A and the second longitudinal edge 75B of the chassis 140 such that neither the first segment 181 nor the second segment 182 extend beyond the first longitudinal edge 75A or the second longitudinal edge 75B. Alternatively, the first segment 181 and/or the second segment 182 can extend beyond one or both of the first longitudinal edge 75A and the second longitudinal edge 75B. For example, the first segment 181 and/or the second segment 182 can extend to an outer edge of the front side panels 124 and/or the back side panels 130, respectively.

The first segment 181 and/or the second segment 182 can extend longitudinally outward beyond the front waist edge 50 and the back waist edge 51, respectively, such that at least a region of the first segment 181 and/or a region of the second segment 182 is visible from a vantage point which is external to the disposable absorbent article 100. The first segment 181 and the second segment 182 may be of any suitable length. For example, the first segment 181 can have a length 198 ranging from about 10 mm to about 75 mm or any individual number within the range. The second segment 182 can be configured similar to the first segment 181. Embodiments are contemplated where the waist member 180 comprises the first segment 181 independently of the second segment 182 or vice versa.

FIG. 2A is an exaggerated cross sectional view showing the disposable absorbent article 100 through section line 2A-2A in the back waist region 108 (see FIG. 1B). As shown, a portion of the back side panels 130 can be disposed between the topsheet 170 and the backsheet 174. The back side panels 130 can extend outboard of the longitudinal edges 75A and 75B and can also have a portion inboard of the longitudinal edges 75A and 75B which is attached to the backsheet 174, the topsheet 170, or both.

The back attachment elements 12 can be disposed on an outer-facing surface 217 of the disposable absorbent article 100. Similarly, the second segment 182 may optionally comprise attachment elements 12B which are attached to an outer-facing surface 221 of the second segment 182. The back attachment elements 12B can allow the second segment 182 to attach to the first segment 181 (see FIG. 1B) such that the waist member 180 (see FIG. 1A) can encircle the waist of the wearer.

The second segment 182 of the waist member can be disposed on a wearer-facing surface 215 of the disposable absorbent article 100. The second segment 182 can extend laterally beyond the first longitudinal edge 75A and the second longitudinal edge 75B of the chassis 140 such that the second segment 182 is coextensive with each of the back side panels 130. The second segment 182 can be attached to a portion of the topsheet 170 and portions of each of the pair of back side panels 130. The second segment 182 can be attached to the chassis in any suitable location such that at least a portion of the front waist edge 50 and/or a portion of the rear waist edge 51 (see FIGS. 1A and 1B) of the disposable absorbent article 100 are provided with a finished appearance.

FIG. 2B is an exaggerated cross sectional view showing a disposable absorbent article 100B constructed in accordance with the present invention. Similar to the cross section shown in FIG. 2A, the back side panels 130 can be disposed between the topsheet 170 and a backsheet 174 and attached to either the topsheet 170, the backsheet 174, or both. However, as shown, the backsheet 174 can be coextensive with the back side panels 130 and extend to an outer edge 202 of the back side panels 130. The topsheet 170 can also be generally coextensive with the back side panels 130 in certain embodiments.

As shown, the back attachment elements 12 can be disposed on the outer-facing surface 217 of the disposable absorbent article 100B. Similarly, the second segment 182 may optionally comprise attachment elements 12B which are attached to the outer-facing surface 221 of the second segment 182.

The second segment 182 of the waist member 180 (see FIG. 1), similar to the embodiment of FIG. 2A, can be disposed on the wearer-facing surface 215 of the disposable absorbent article 100B. The second segment 182 can be attached to a portion of the topsheet 170 and/or a portion of the back side panels 130.

FIG. 2C is an exaggerated cross sectional view of a disposable absorbent article 100C which is constructed in accordance with the present invention. The disposable absorbent article 100C may comprise an outer cover 1040 which includes a first backsheet layer 241, a front waist region, a back waist region, and a crotch region disposed therebetween. The disposable absorbent article 100C may further comprise an absorbent assembly 1050. The absorbent assembly 1050 may include a first longitudinal edge 275A and a second longitudinal edge 275B. The absorbent assembly 1050 may also include the topsheet 170, a second backsheet layer 242, and the absorbent core 178 (see FIG. 1B). The absorbent assembly 1050 can be joined to the wearer-facing surface 1015 of the disposable absorbent article 100C. The absorbent assembly 1050 can be joined to the outer cover 1040 such that the first longitudinal edge 275A is spaced apart from a first back side panel 230A by a first gap 280 and the second longitudinal edge 275B is spaced apart from a second back side panel 230B by a second gap 282.

The disposable absorbent article 100C may further comprise at least two barrier leg cuffs 252 and 254 attached to the topsheet 170 adjacent to the longitudinal edges 275A and 275B of the absorbent assembly 1050. The barrier leg cuffs 252 and 254 can also be attached to the first backsheet layer 241.

The barrier leg cuff 252 comprises a distal region 260 and a proximal region 265 while the barrier leg cuff 254 comprises a distal region 267 and a proximal region 266. The proximal region 265 of the barrier leg cuff 252 can be attached to a first back side panel 230A and the first backsheet layer 241 in an overlapping manner. Similarly, the proximal region 266 of the barrier leg cuff 254 can be attached to a second back side panel 230B and the first backsheet layer 241 in an overlapping manner. The distal region 260 of the barrier leg cuff 252 can be attached to the topsheet 170 and the second backsheet layer 242. Similarly, the distal region 267 of the barrier leg cuff 254 can be attached to the topsheet 170 and the second backsheet layer 242.

As shown, the second segment 182 can be attached to the barrier leg cuffs 252 and 254 adjacent to the distal regions 260 and 267 and proximal regions 265 and 266. As shown, the second segment 182 can also be attached to a portion of the first back side panel 230A and a portion of the second back side panel 230B. Also, the second segment 182 can be coextensive with the first back side panel 230A and the second back side panel 230B such that the second segment 182 extends to outer edges 202A and 202B of the first and second back side panels 230A and 230B. The second segment 182 is not required to be coextensive with the outer edges 202A and 202B of the first and second back side panels 230A and 230B.

As shown, the barrier leg cuffs 252 and 254 can be attached to the first backsheet layer 241 between their attachment to the back side panels 230A and 230B, respectively, and the second backsheet layer 242. The attachment of the barrier leg cuffs 252 and 254 to the first backsheet layer 241 can define the first gap 280 and the second gap 282. The first gap 280 can extend longitudinally for a length of the first back side panel 230A. Similarly, the second gap 282 can extend longitudinally for a length of the second back side panel 230B. The first gap 280 can define a width of a first non-elastic region 271 of the disposable absorbent article 100C disposed between the first back side panel 230A and the second backsheet layer 242, and the second gap 282 can define a width of a second non-elastic region 272 of the disposable absorbent article 100C disposed between the second back side panel 230B and the second backsheet layer 242.

The inclusion of the non-elastic regions 271 and 272 can offer many advantages over previous disposable pant-type garments, such as pull-on diapers. For example, the inclusion of the non-elastic regions 271 and 272, when the first back side panel 230A and the second back side panel 230B comprise high quality elastomeric materials, can mean a cost savings. This savings in elastomeric materials can translate to a significant cost savings for disposable pull-on garments, which are produced in the hundreds of thousands, if not more, daily. That is, the amount of elastomeric material used in the first back side panel 230A, the second back side panel 230B, and the front side panels of the disposable absorbent article is minimized, while the disposable absorbent article still provides comparable, if not superior, fit and stretch to prior disposable pant-type garments.

The first and second gaps 280 and 282 may be of any suitable width in a lateral direction 299. For example, in one embodiment, the first and the second gaps 280 and 282 may range in width from about 0.5 mm to about 26 mm or any individual number within the range. In another embodiment, the first and the second gaps 280 and 282 may range in width from about 0.5 mm to about 20 mm. In yet another embodiment, the first and the second gaps 280 and 282 may range in width from about 1 mm to about 15 mm. The first gap 280 and the second gap 282, along with the non-elastic regions 271 and 272, are discussed in U.S. Patent Application Publication No. 2004/0225273.

As shown, the back attachment elements 12 can be disposed on an outer-facing surface 217 of the disposable absorbent article 100C. Similarly, the second segment 182 may optionally comprise attachment elements 12B which are attached to an outer-facing surface 221 of the second segment 182.

The barrier leg cuffs 252 and 254 of FIG. 2C can provide improved containment of liquids and other body exudates. In addition, these barrier leg cuffs 252 and 254 may include several different embodiments for reducing the leakage of body exudates in the leg regions. Illustrative examples of suitable barrier leg cuffs for use in the present invention may be found in U.S. Pat. No. 3,860,003, U.S. Pat. No. 4,909,803, U.S. Pat. No. 4,695,278, U.S. Pat. No. 4,795,454, U.S. Pat. No. 4,704,115, and U.S. Pat. No. 4,808,178.

In addition, the barrier leg cuffs 252 and 254 may be attached to the disposable absorbent article 100C by any suitable attachment means or any suitable combination of attachment means known in the art. Some examples of suitable attachment means include, but are not limited to, adhesive bonds, heat bonds, pressure bonds, ultrasonic bonds, and dynamic mechanical bonds. Additionally, in some embodiments, it may be desirable to treat all or a portion of the leg cuffs with a lotion or a fecal modification agent which either increases or decreases the Hardness of fecal material which it encounters. Lotions as well as fecal modification agents are discussed in U.S. Patent Publication No. 2004/0039362A1 and U.S. Pat. No. 6,639,119.

FIGS. 2A-2C provide illustrative examples of where the second segment 182 can be attached to a disposable absorbent article. The second segment 182 can be attached to a disposable absorbent article in any suitable location and by any suitable means. In addition, while the second segment 182 can be a continuous element which extends laterally across a disposable absorbent article from one end to the other end of the disposable absorbent article, the second segment 182 is not required to be continuous nor is the second segment 182 required to extend from one end to the other end of the disposable absorbent article.

Figure 2D:
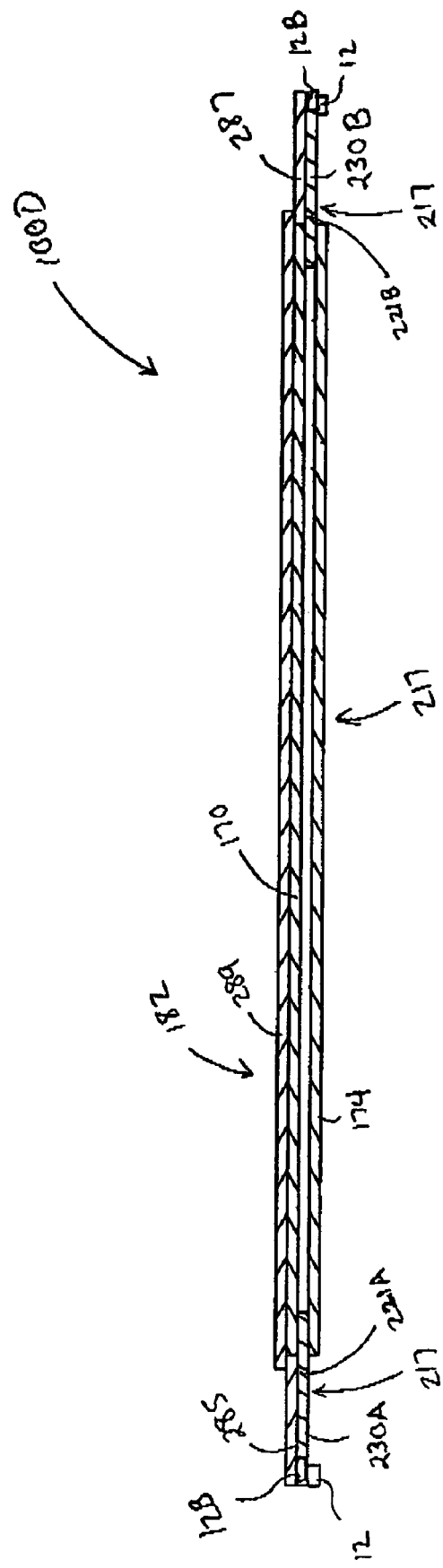

As shown in FIG. 2D, for example, a disposable absorbent article 100D comprises the second segment 182 of the waist member 180 (see FIGS. 1A and 1B) which includes a plurality of discrete elements. As shown, the second segment 182 may comprise a first waist element 285 which may be attached to a first back side panel 230A and a second waist element 287 which may be attached to a second back side panel 230B. The second segment 182 may further comprise a third waist element 289 which may be attached to a portion of a topsheet 170. The first waist element 285, second waist element 287, and the third waist element 289, can be disposed adjacent to the back waist edge 51 (see FIG. 1B) and can be attached to one another in an overlapping manner.

The back attachment elements 12 can be disposed on the outer-facing surface 217 of the disposable absorbent article 100D. Similarly, the first waist element 285 and the second waist element 287 may optionally comprise attachment elements 12B which are attached to an outer-facing surface 221A of the first waist element 285 and an outer-facing surface 221B of the second waist element 287. Embodiments are contemplated where the first waist element 285, the second waist element 287, and/or the third waist element 289 are disposed between the topsheet 170 and the backsheet 174.

The first segment 181 (see FIG. 1B) of the waist member can be situated in the front waist region as described above in regard to the second segment 182 of the waist member. Additionally, in any of the embodiments discussed herein, the first segment 181 or the second segment 182 may comprise a plurality of discrete elements as discussed above in regard to FIG. 2D. Embodiments are contemplated where the first segment 181 and/or the second potion 182 comprise more than three waist elements or less than three waist elements.

As shown in FIG. 3A, the first segment 181 of the waist member 180 can be attached to a portion of the topsheet 170 adjacent to the front waist edge 50 on the wearer facing surface 215 of the disposable absorbent article 100. The first segment 181 may comprise a visible region 181A and an attachment region 181B. The first segment 181 can be attached to a portion of the topsheet 170 such that the visible region 181A is visible from a vantage portion external to the disposable absorbent article 100. The attachment region 181B is not necessarily visible from the external vantage point through the topsheet 170 and the backsheet 174. In this embodiment, because the first segment 181 is attached to the wearer-facing surface 215 of the disposable absorbent article 100, the skin of the lower torso of the wearer is protected from at least a portion of the front waist edge 50.

The visible region 181A can extend beyond the front waist edge 50 by a distance 390 measured generally parallel to a longitudinal direction 399. In some embodiments, the distance 390 may range from about 0 mm to about 50 mm or any individual number within the range. In other embodiments, the distance 390 can be greater than about 2 mm. In other embodiments, the distance 390 can be greater than about 15 mm. In yet other embodiments, the distance 390 can be greater than about 30 mm.

Distinctions can be made between absorbent articles for boys and absorbent articles for girls. For example, the visible region 181A on a disposable absorbent article for boys may extend beyond a waist edge of the disposable absorbent article by the distance 390 of 50 mm. In some embodiments, in a disposable absorbent article for boys, the distance 390 can be greater than or equal to 15 mm and less than or equal to 50 mm or any individual number in the range. In contrast, the visible region 181A in a disposable absorbent article for girls may extend beyond the waist edge of the disposable absorbent article by the distance 390 of less than about 30 mm. For example, in some embodiments, the distance 390, in a disposable absorbent article for girls, can be greater than about 0 mm and less than or equal to about 20 mm or any individual number within the range.

Figure 3B:
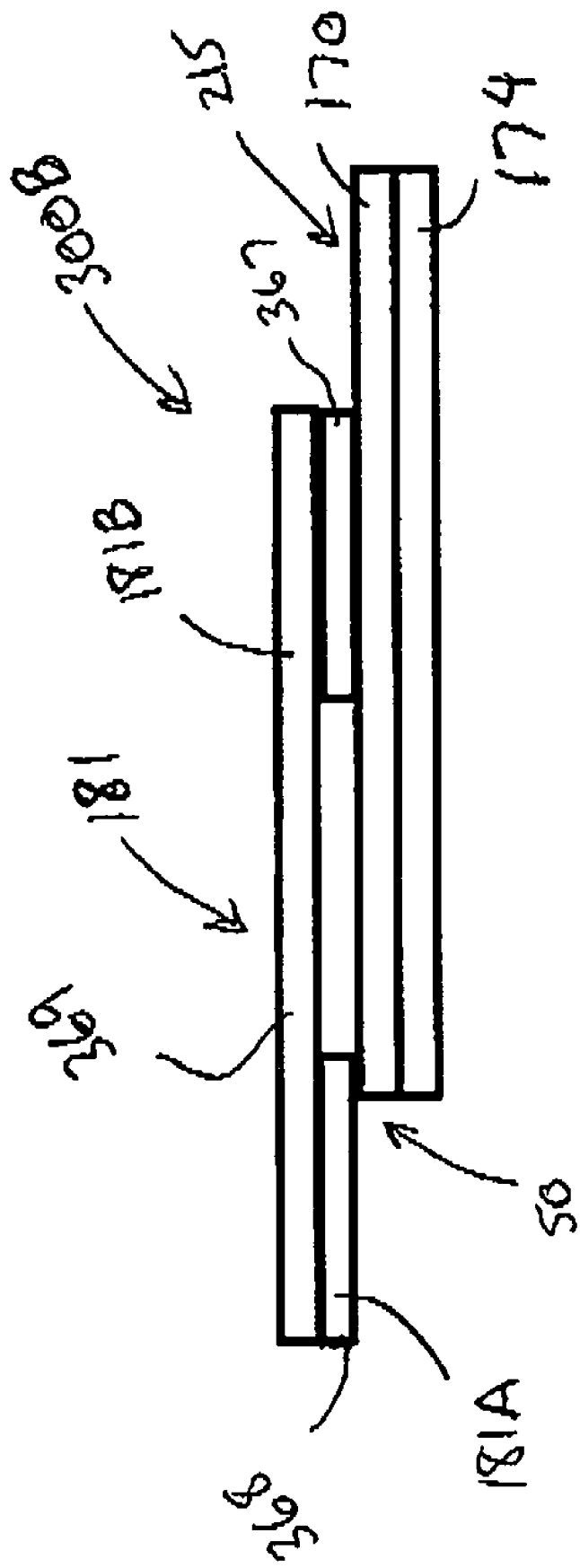

As shown in FIG. 3B, in some embodiments, the first segment 181 may comprise a plurality of discrete parts. For example, the first segment 181 may include a first elastic region 367 disposed on the wearer-facing surface 215 of a disposable absorbent article 300B. Similarly, a portion of a second elastic region 368 can be disposed on the wearer-facing surface 215 of the disposable absorbent article 300B. A non-elastic linking element 369 can be attached to both the first elastic region 367 and the second elastic region 368. Embodiments are contemplated where the first elastic region 367, the second elastic region 368, and the linking element 369 are disposed between the topsheet 170 and the backsheet 174.

In some embodiments, the attachment region 181B may comprise the first elastic region 367 and a portion of the non-elastic linking element 369. In contrast, in some embodiments, the visible region 181A may comprise the second elastic region 368 and a portion of the non-elastic linking element 369.

In one particular embodiment, one advantage is that when the first segment 181 and the second segment are attached, the first elastic region 367, the second elastic region 368, and the non-elastic linking element 369 can form a belt like structure about a wearer's waist. The first elastic region 367 and the second elastic region 368 can be provided with different elastic moduli such that the article provides a better fit for a wearer.

As shown in FIG. 3C, the first segment 181 can be attached between the topsheet 170 and the backsheet 174 of a disposable absorbent article 300C. Similar to the embodiment shown in FIG. 3A, the visible region 181A can extend outward from the front waist edge 50 by the distance 390 as described in regard to FIG. 3A.

Because the first segment 181 and the second segment 182 (see FIG. 1B) can be attached to a wearer-facing surface of a disposable absorbent article or between the topsheet 170 and the backsheet 174, the disposable absorbent article can be provided with an appearance of a finished front waist edge 50 and/or an appearance of a finished back waist edge 51 (see FIG. 1B). Additionally, because the first segment 181 and the second segment 182 (see FIG. 1B) are not attached to an outer-facing surface of the disposable absorbent article, the process for attaching the first segment 181 and the second segment 182 (see FIG. 1B) to the disposable absorbent article is facilitated. For example, the neither the first segment 181 nor the second segment 182 (see FIG. 1B) have to be folded about the front waist edge 50 or the back waist edge 51 (see FIG. 1B), thereby facilitating the process for applying the waist member 180 to the disposable absorbent article.

Figure 3D:
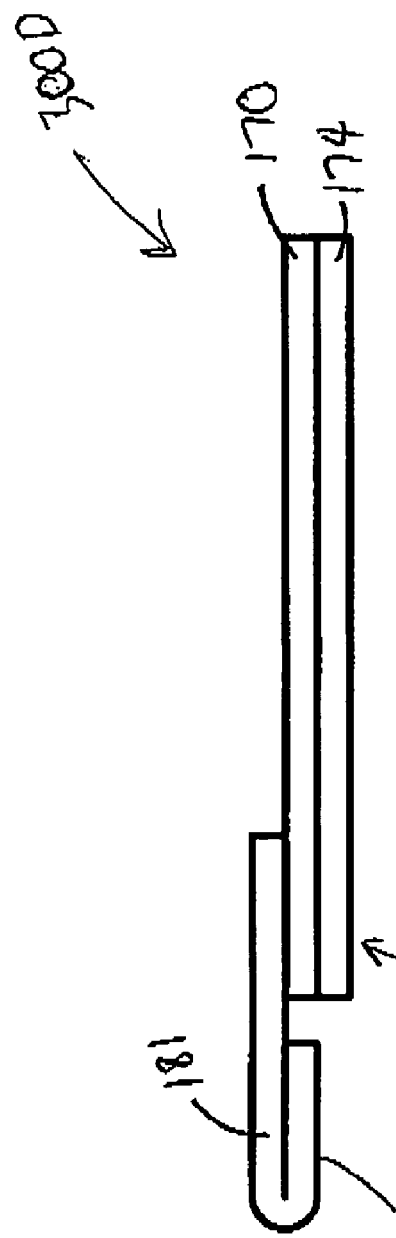
Figure 3E:
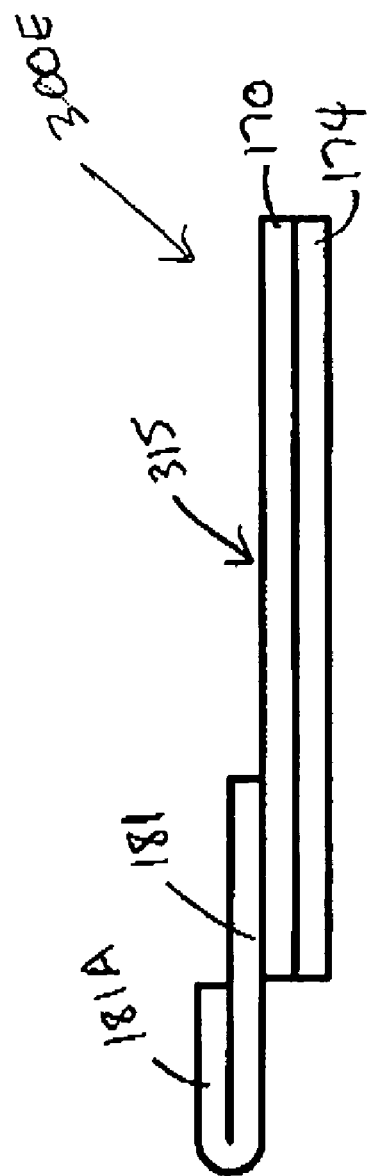

Regarding FIGS. 3D and 3E, regardless of whether the first segment 181 is disposed on a wearer-facing surface of a disposable absorbent article or between a topsheet 170 and a backsheet 174 of the disposable absorbent article, the visible region 181A of the first segment 181 can be configured in many different ways. As shown in FIG. 3C, for example, the visible region 181A can be folded onto the first segment 181 on the outer-facing surface 217 of a disposable absorbent article 300D. As shown in FIG. 3D, as another example, the visible region 181A of the first segment 181 can be folded onto the first segment 181 on the wearer-facing surface 315 of the disposable absorbent article 300E.

In any of the embodiments discussed herein, the waist member can be dyed or otherwise colored such that the visible region and the attachment region comprise a different color than that of the backsheet and the topsheet. For example, the visible region and/or the attachment region can comprise a color and/or a graphic. In some embodiments, the color and/or graphic of the attachment region can be configured such that the color and/or the graphic appear through the topsheet and the backsheet. The color can be associated with the gender of a wearer. For example, in an absorbent article for girls, the visible region and/or the attachment region may comprise a color which includes a shade of pink. As another example, in an absorbent article for boys, the visible region and/or the attachment region may comprise a color which includes a shade of blue. In yet another example, the visible region and/or the attachment region may comprise a color which is gender neutral, such as shades of purple or shades of green. Further examples are discussed in U.S. Patent Publication No. 2005/0129743A1, U.S. Patent Publication No. 2005/0125923A1, and U.S. Patent Publication No. 2005/0125877A1.

In conjunction with or independent from the color, the first segment may comprise a graphic or child graphic in the visible region and/or the attachment region. The graphic may be any suitable visual image or images. The graphic may include pictorial symbols and/or images, such as, but not limited to, photographs, drawings, embossments, or any other suitable materials utilized to create pictorial symbols and/or images. The pictorial symbols and/or images may include an image of a child, an anthropomorphic image of an animal or object, images of cartoons including well known cartoon characters, images of well known brand logos or the like, and/or images characters specifically created to be associated with the implement of commerce, symbols, such as, but not limited to arrows, indications or motion or movement, and the like, and combinations thereof. Graphics and child graphics are discussed in U.S. Patent Publication No. 2005/0129743A1, U.S. Patent Publication No. 2005/0125923A1, and U.S. Patent Publication No. 2005/0125877A1.

Processes for coloring the waist member 180 are discussed in U.S. Pat. No. 4,089,765, U.S. Pat. No. 5,989,380, U.S. Pat. No. 6,548,431, and WO 2004/071780. Processes suitable for adding graphics to the waist member 180 are also discussed in these documents.

In conjunction with or independent from the color and/or graphics discussed above, the waist member may comprise texture features. Texture features can impart a unique visual appearance and/or a tactile difference to the waist member, such as by forming layers, regions of relative smoothness or roughness, varying reflectivity, color enhancements, or other visual effect. Examples of suitable processes for forming texture features include mechanical treatment (such as embossing, ring rolling, bonding, scoring, puncturing, or slitting), and non-mechanical treatments such as laser, hot air, chemical, or other processes.

Each of the mechanical treatments may result in particular types of texture features. For example, embossing may be performed either hot or cold, with either a smooth or a patterned roll, and may result in projections, recesses, areas of relative smoothness, areas of compression (and associated compression resistance), or combinations thereof. In another example, ring rolling may result in openings, projections, recesses, or combinations thereof. In yet another example, methods for forming structural elastic-like film (SELF) may be employed, such as those disclosed in U.S. Pat. No. 5,554,143 issued to Roe et al. on Sep. 10, 1996 entitled "Absorbent Article with Multiple Zone Structural Elastic-Like Film Web Extensible Waist Feature" and U.S. Pat. No. 5,518,801 issued to Chappell et al. on May 21, 1996 entitled "Web Materials Exhibiting Elastic-Like Behavior", and may result in projections, recesses, or combinations thereof. In yet another example, scoring may cause surface morphology such as areas of relative roughness or fuzziness. In yet another example, puncturing may cause openings at least partially surrounded by three-dimensional projections.

Other exemplary processes for creating texture features may include forming the waist member from a material having a higher basis weight or a lower basis weight than the basis weight of a backsheet, a topsheet, front side panels, and/or back side panels, of a disposable absorbent article to which the waist member is attached. Other exemplary processes may include forming the waist member from a material having a higher denier or a lower denier than the denier of a backsheet, a topsheet, front side panels, and/or back side panels, of a disposable absorbent article to which the waist member is attached. Any suitable processes known in the art for providing the waist member with a texture feature can be used.

Figure 4B:
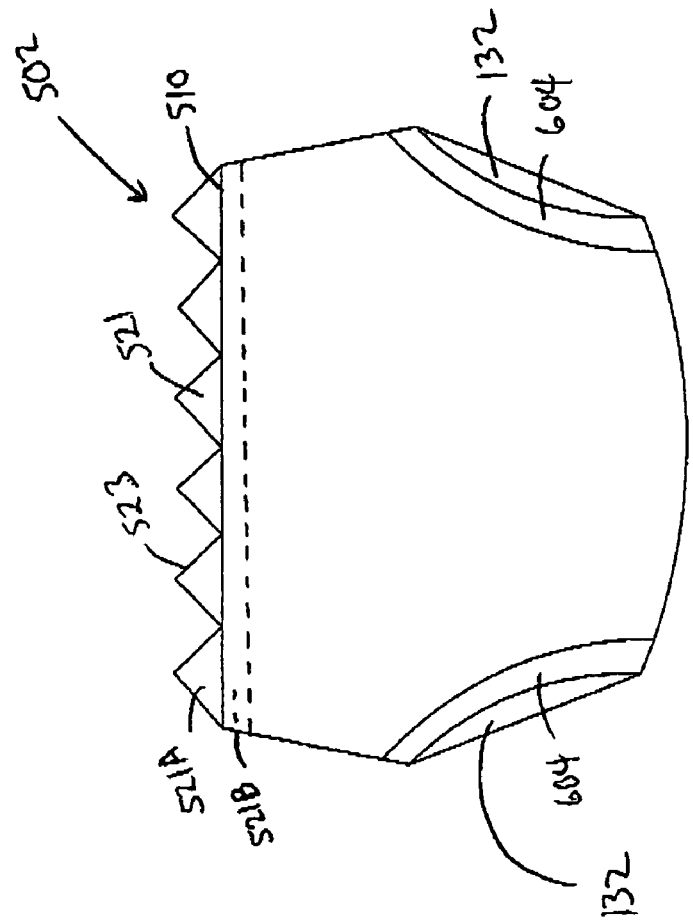
FIGS. 4A-4B are elevation views of other embodiments of disposable absorbent articles constructed in accordance with the present invention.
Figure 4A:
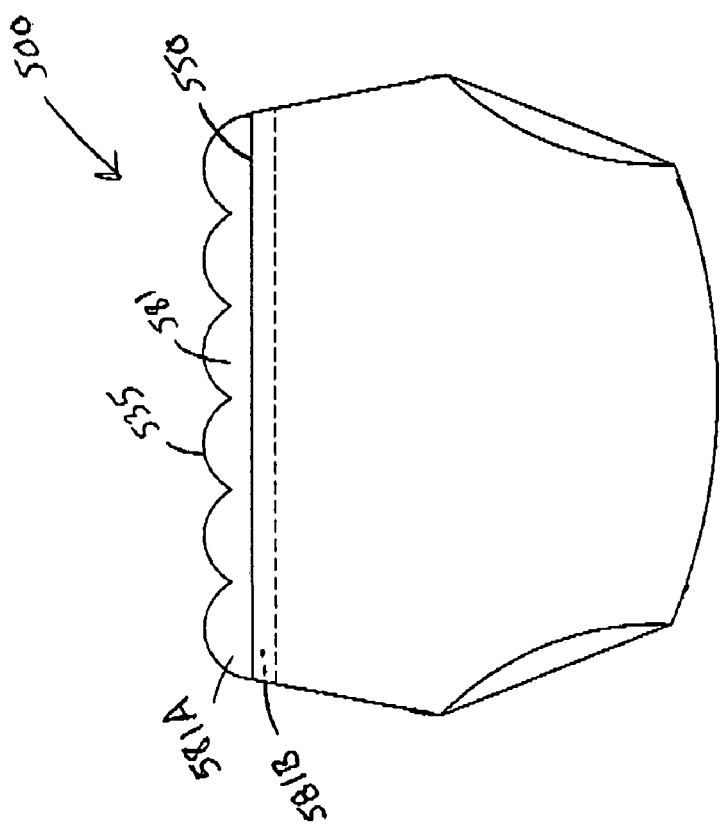

Additionally, the waist member can be configured such that an outer edge of the first segment, the second segment, or both, is non-uniform. As shown in FIGS. 4A and 4B, the outer edge of the first segment, the second segment, or both may utilize any suitable shape known in the art. For example, in an absorbent article for girls, the outer surface may comprise a scalloped outer edge. As another example, an absorbent article for boys may comprise a serrated outer edge. Also, a disposable absorbent article constructed in accordance with the present invention may comprise a waist member which utilizes a combination of suitable shapes and/or having varying sized shapes for its outer edge.

As shown in FIG. 4A, a disposable absorbent article 500 may comprise a first segment 581 of a waist member 180 (see FIG. 1A). The first segment 581 can have a visible region 581A disposed above a front waist edge 550 and a attachment region 581B disposed below the front waist edge 550. Additionally, the first segment 581 may further comprise a scalloped outer edge 535. The visible region 581A, the attachment region 581B, the color, dye, graphics, or any combination thereof, may comprise a plurality of apertures to appear more lace-like.

As shown in FIG. 4B, a disposable absorbent article 502 may comprise a first segment 521 of a waist member 180 (see FIG. 1A). The first segment 521 can have a visible region 521A disposed above a front waist edge 510 and a attachment region 521B disposed below the front waist edge 510. The first segment 521 may further comprise a serrated outer edge 523.

In addition, the disposable absorbent article 502 may further comprise edge members 604. The edge members can be disposed along the longitudinal edges of the disposable absorbent article 502 and can provide a pair of leg openings 132 with a finished look. The edge members 604 and a method of applying the edge members 604 are discussed in U.S. Patent Publication No. 2003/0088227A1. The edge members 604 can be utilized with any of the embodiments of the disposable absorbent articles discussed herein. Additionally, the edge members 604 can be dyed, colored, provided with texture features, or any combination thereof, as described above.

Figure 5:
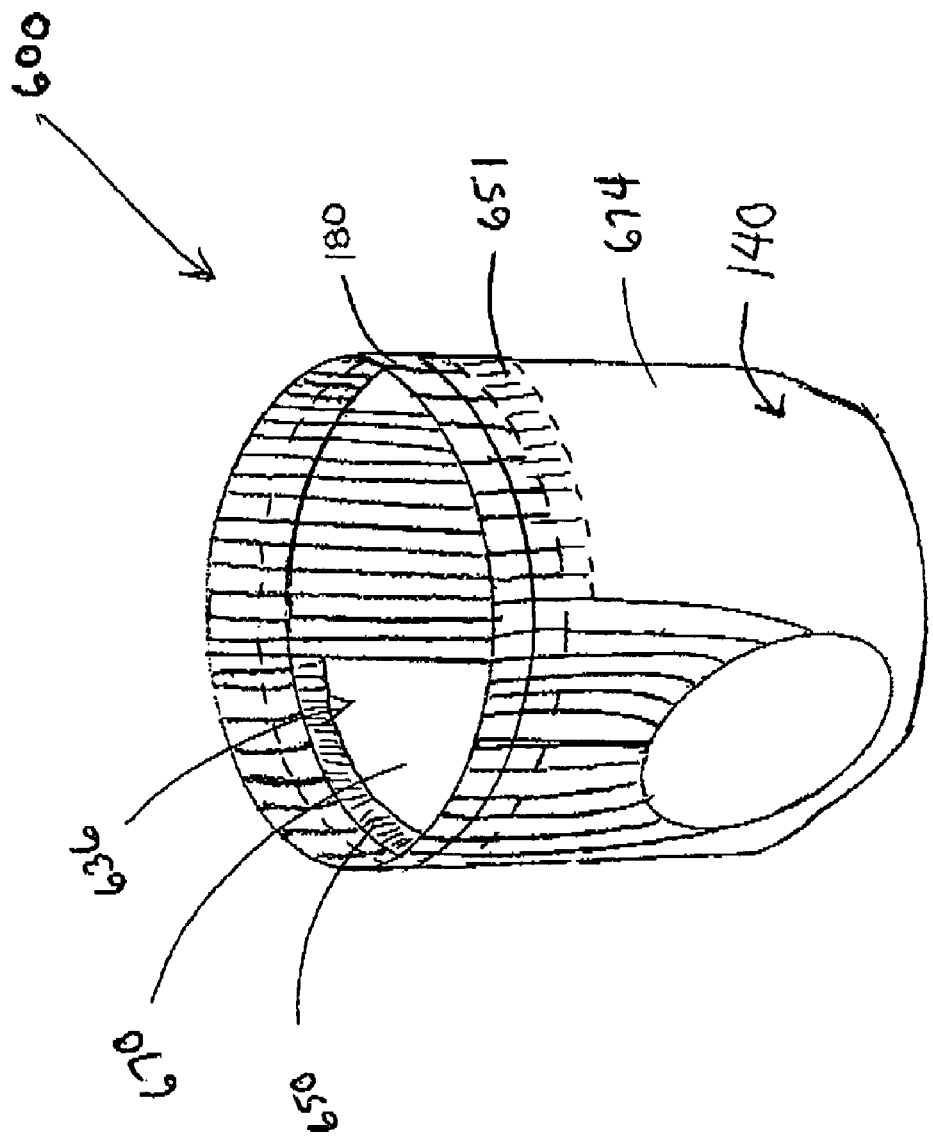
FIG. 5 is another embodiment of a disposable absorbent article constructed in accordance with the present invention.

As shown in FIG. 5, in another embodiment, a disposable absorbent article 600 constructed in accordance with the present invention may further comprise, in addition to the chassis 140, a front elastic member 650 and a back elastic member 651 which are disposed adjacent to the waist member 180. The front elastic member 650 and the back elastic member 651 can be elastically extensible and can allow a waist opening 636 of the disposable absorbent article 600 to expand and contract about the waist of a wearer. The front elastic member 650 can be disposed in a front waist region, and the second elastic member 651 can be disposed in a back waist region. As shown, the front elastic member 650 is disposed on a topsheet 670 of the disposable absorbent article 600. In other embodiments, the front elastic member 650 and the back elastic member 651 can be disposed between the topsheet 670 and a waist member 180 or the topsheet 670 and a backsheet 674. The front elastic member 650 and the back elastic member 651 may be disposed in the disposable absorbent article 600 in a number of different configurations. Examples of suitable configurations for both the front elastic member 650 and the back elastic member 651 are described in U.S. Pat. No. 4,515,595, U.S. Pat. No. 4,710,189, U.S. Pat. No. 5,151,092, and U.S. Pat. No. 5,221,274.

A disposable absorbent article of the present invention, as discussed previously, comprises many different members/elements, e.g. a waist member, a topsheet, a backsheet, an absorbent core, etc. for which a wide assortment of materials can be used. For example, any suitable material can be used for the waist member. The waist member can be compliant and soft. Additionally, because the waist member can contact the skin of the wearer, the waist member can also be non-irritating to the skin of the wearer. Exemplary waist members can comprise nonwoven. A suitable nonwoven may comprise fibers made of polypropylene, polyethylene, polyester, nylon, cellulose, polyamide, or combinations of such materials. Fibers of one material or fibers of different materials or material combinations may be used in the first and/or second nonwoven. Exemplary nonwoven materials include spunbond, spunbond meltblown spunbond (SMS), spunbond meltblown meltblown spunbond (SMMS), carded and the like. Particularly acceptable nonwovens include high elongation carded (HEC) nonwovens and deep activation polypropylene (DAPP) nonwovens. Any process known in the art may be used to make the nonwovens.

The nonwoven may comprise fibers that are bonded internally, including fibers that are needle punched, hydro entangled, spun bonded, thermally bonded, bonded by various types of chemical bonding such as latex bonding, powder bonding, and the like. In certain embodiments, the basis weight of the nonwoven can be in the range of about 10 gsm to about 40 gsm or any individual number within the range.

The fibers may be of any suitable size. In some embodiments, the fiber may have a denier ranging from about 1 to about 10 or any individual number within the range. In some embodiments, the denier of the fibers can range from about 1 to about 8. In other embodiments, the denier of the fibers can range from about 1 to about 5.

As discussed previously, a waist member, in accordance with the present invention, can be elastically extensible. So, the waist member may further comprise any elastic material known in the art. Examples of suitable elastic materials may include elastic strands or elastic films. Any suitable elastic film known in the art can be used. Examples of suitable elastic films may comprise polypropylene, polyethylene, polyolefins, styrene-isoprene-styrene, styrene-butadiene-styrene, or combinations thereof.

Any topsheet compatible with the present invention which is known in the art can be used in the present invention. A suitable material for a topsheet may be manufactured from a wide range of materials, such as porous foams, reticulated foams, apertured plastic films, or woven or nonwoven materials of natural fibers (e.g., wood or cotton fibers), synthetic fibers (e.g., polyester or polypropylene fibers), or a combination of natural and synthetic fibers. As an example, a material suitable for use in a topsheet comprises a web of staple-length polypropylene fibers is manufactured by Veratec, Inc., a Division of International Paper Company, of Walpole, Mass. under the designation P-8.

Some examples of suitable topsheets are described further in U.S. Pat. No. 3,929,135; U.S. Pat. No. 4,324,246; U.S. Pat. No. 4,342,314; U.S. Pat. No. 4,463,045; U.S. Pat. No. 5,006,394; U.S. Pat. No. 4,609,518; U.S. Pat. No. 4,629,643. Any portion of the topsheet may be coated with a lotion as is known in the art. Examples of suitable lotions include those described in U.S. Pat. No. 5,607,760; U.S. Pat. No. 5,609,587; U.S. Pat. No. 5,635,191; U.S. Pat. No. 5,643,588; U.S. Pat. No. 5,968,025; U.S. Pat. No. 6,716,441; and PCT Publication No. WO 95/24173.

Further, the topsheet may be fully or partially elastically extensible or may be foreshortened so as to provide a void space between the topsheet and the absorbent core. Exemplary structures including elasticized or foreshortened topsheets are described in more detail in U.S. Pat. No. 4,892,536; U.S. Pat. No. 4,990,147; U.S. Pat. No. 5,037,416; and U.S. Pat. No. 5,269,775.

A suitable backsheet for use in the disposable absorbent article of the present invention may comprise a laminated structure. For example, as previously discussed, the backsheet may comprise a first backsheet layer and a second backsheet layer (see items 241 and 242 of FIG. 2C). The second backsheet layer can be impervious to liquids (e.g., urine) and comprise a thin plastic film such as a thermoplastic film having a thickness, for example, of about 0.012 mm (0.5 mil) to about 0.051 mm (2.0 mils). Suitable backsheet films include those manufactured by Tredegar Corporation, based in Richmond, Va., and sold under the trade name CPC2 film. Either the first backsheet layer and/or the second backsheet layer may include breathable materials which permit vapors to escape from the pull-on garment while still preventing exudates from passing through the backsheet. Suitable breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va. and sold under the designation EXAIRE, and monolithic films such as manufactured by Clopay Corporation, Cincinnati, Ohio under the name HYTREL blend P18-3097. Some breathable composite materials are described in greater detail in PCT Application No. WO 95/16746; U.S. Pat. No. 5,938,648; U.S. Pat. No. 5,865,823; and U.S. Pat. No. 5,571,096.

The backsheet, or any portion thereof, may be elastically extensible in one or more directions. In one embodiment, the backsheet may comprise a structural elastic-like film ("SELF") web. A structural elastic-like film web is an extensible material that exhibits an elastic-like behavior in the direction of elongation without the use of added elastic materials and is described in more detail in U.S. Pat. No. 5,518,801. In alternate embodiments, the backsheet may comprise elastic films, foams, strands, or combinations of these or other suitable materials with nonwovens or synthetic films.

A suitable absorbent core for use in the present invention may comprise any absorbent material which is generally compressible, conformable, non-irritating to the wearer's skin, and capable of absorbing and retaining liquids such as urine and other certain body exudates. In addition, the configuration and construction of the absorbent core may also be varied (e.g., the absorbent core(s) or other absorbent structure (s) may have varying caliper zones, hydrophilic gradient(s), a superabsorbent gradient(s), or lower average density and lower average basis weight acquisition zones; or may comprise one or more layers or structures). Suitable exemplary absorbent structures for use as the absorbent core are described in U.S. Pat. No. 4,610,678; U.S. Pat. No. 4,673,402; U.S. Pat. No. 4,834,735; U.S. Pat. No. 4,888,231; U.S. Pat. No. 5,137,537; U.S. Pat. No. 5,147,345; U.S. Pat. No. 5,342,338; U.S. Pat. No. 5,260,345; U.S. Pat. No. 5,387,207; and U.S. Pat. No. 5,625,222.

The backsheet may be attached to the topsheet, the absorbent core, or any other element of the disposable absorbent article by any attachment means known in the art. For example, the attachment means may include a uniform continuous layer of adhesive, a patterned layer of adhesive, or an array of separate lines, spirals, or spots of adhesive. Some suitable attachment means are disclosed in U.S. Pat. No. 4,573,986; U.S. Pat. No. 3,911,173; U.S. Pat. No. 4,785,996; and U.S. Pat. No. 4,842,666. Examples of suitable adhesives are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

The fastening elements discussed herein preferably maintain the front waist region and the back waist region in a configuration so as to provide lateral tensions about the circumference of the disposable absorbent article to hold the disposable absorbent article on the wearer. The fastening elements preferably comprise a surface fastener such as tape tabs, hook and loop fastening components, hook and hook, and/or hermaphroditic fastening components, although any other known fastening means are generally acceptable. In alternative embodiments, opposing sides of the article may be seamed or welded to form a pant. This can allow the article to be used as a pull-on type diaper, such as a training pant.

Some exemplary surface fastening systems are disclosed in U.S. Pat. No. 3,848,594, U.S. Pat. No. 4,662,875, U.S. Pat. No. 4,846,815, U.S. Pat. No. 4,894,060, U.S. Pat. No. 4,946,527, U.S. Pat. No. 5,151,092, and U.S. Pat. No. 5,221,274. An exemplary interlocking fastening system is disclosed in co-pending U.S. Pat. No. 6,432,098. The fastening system may also: provide a means for holding the article in a disposal configuration as disclosed in U.S. Pat. No. 4,963,140; include primary and secondary fastening systems, as disclosed in U.S. Pat. No. 4,699,622; provide means to reduce shifting of overlapped portions or to improve fit as disclosed in U.S. Pat. No. 5,242,436; and provide means to resist gapping at a wearer's belly as disclosed in U.S. Pat. No. 5,499,978, U.S. Pat. No. 5,507,736, and in U.S. Pat. No. 5,591,152.

Various sublayers may be disposed between the topsheet and the backsheet. The sublayer may be any material or structure capable of accepting, storing or immobilizing bodily exudates. Thus, the sublayer may include a single material or a number of materials operatively associated with each other. Further, the sublayer may be integral with another element of the pull-on disposable absorbent article or may be one or more separate elements attached directly or indirectly with one or more elements of the disposable absorbent article. Further, the sublayer may include a structure that is separate from the absorbent core or may include or be part of at least a portion of the absorbent core.

Suitable exemplary materials for use as the sublayer may include large cell open foams, macro-porous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibers, absorbent core structures described above having punched holes or depressions, and the like. (As used herein, the term "microporous" refers to materials which are capable of transporting fluids by capillary action. The term "macroporous" refers to materials having pores too large to effect capillary transport of fluid, generally having pores greater than about 0.5 mm in diameter and, more specifically, having pores greater than about 1.0 mm in diameter.) One embodiment of a sublayer includes a mechanical fastening loop landing element, having an uncompressed thickness of about 1.5 millimeters available as XPL-7124 from the 3M Corporation of Minneapolis, Minn. Another embodiment includes a 6 denier, crimped and resin-bonded nonwoven highloft having a basis weight of 110 grams per square meter and an uncompressed thickness of 7.9 millimeters which is available from the Glit Company of Wrens, Ga. Other suitable absorbent and nonabsorbent sublayers are described in U.S. Pat. No. 6,680,422 and U.S. Pat. No. 5,941,864. Further, the sublayer, or any portion thereof, may include or be coated with a lotion or other known substances to add, enhance or change the performance or other characteristics of the element.

Embodiments of the present invention may also include pockets for receiving and containing waste, spacers which provide voids for waste, barriers for limiting the movement of waste in the article, compartments or voids which accept and contain waste materials deposited in the pull-on disposable absorbent article, and the like, or any combinations thereof. Examples of pockets and spacers for use in absorbent products are described in U.S. Pat. No. 5,514,121; U.S. Pat. No. 5,171,236; U.S. Pat. No. 5,397,318; U.S. Pat. No. 5,540,671; U.S. Pat. No. 6,168,584; U.S. Pat. No. 5,306,266; and U.S. Pat. No. 5,997,520. Examples of compartments or voids in an absorbent article are disclosed in U.S. Pat. No. 4,968,312; U.S. Pat. No. 4,990,147; U.S. Pat. No. 5,062,840; and U.S. Pat. No. 5,269,755. Examples of suitable transverse barriers are described in U.S. Pat. No. 5,554,142; PCT Patent WO 94/14395; and U.S. Pat. No. 5,653,703. Examples of other structures suitable for management of low viscosity feces are disclosed in U.S. Pat. No. 5,941,864; U.S. Pat. No. 5,977,430; and U.S. Pat. No. 6,013,063.

Embodiments of the present invention may include acquisition/distribution layers which can be configured to distribute moisture from a wetness event to moisture responsive members within the disposable absorbent article. Examples of suitable acquisition/distribution layers are described in U.S. Pat. No. 5,460,622, U.S. Patent Application Publication No. 2005/0027267, and U.S. Patent Application Publication No. 2005/009173.

Embodiments of the present invention may include a dusting layer which is well known in the art. Examples of suitable dusting layers are discussed in U.S. Pat. No. 4,888,231.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article for wearing about the lower torso of a wearer, the disposable absorbent article having a chassis, a front waist region, a back waist region, and a crotch region disposed between the front and back waist regions, a front waist edge and a back waist edge, wherein the chassis has a periphery that is defined by longitudinal edges and the front waist edge and back waist edge, the disposable absorbent article further comprising:
   a topsheet;
   a backsheet attached to at least a portion of the topsheet;
   an absorbent core disposed between the topsheet and the backsheet, wherein the absorbent core does not extend to the front waist edge and the back waist edge; and
   an elastically extensible waist member,
   a pair of front side panels extending outward from the front waist region and a pair of back side panels extending outward from the back waist region, wherein the pair of front side panels and the pair of back side panels are capable of attaching to each other, thereby forming a waist opening,
   wherein the waist member is attached to each of the pair of front side panels and back side panels and extends to the outer side edges of the front side panels and back side panels,
   and wherein the waist member extends beyond the periphery of the chassis outward from the front waist edge or the back waist edge, such that at least a region of the waist member is visible from a vantage point external to the disposable absorbent article, thereby providing the appearance of a finished front waist edge or the appearance of a finished back waist edge.

2. The disposable absorbent article of claim 1, wherein the waist member comprises a first segment attached to the disposable absorbent article adjacent to the front waist edge, wherein the first segment includes a visible region and an attachment region, wherein the visible region longitudinally extends beyond the front waist edge such that the visible region is visible from an external vantage point, and wherein the visible region comprises a color, a graphic, a texture feature, or a combination thereof.

3. The disposable absorbent article of claim 2, wherein the waist member further comprises a second segment attached to the disposable absorbent article adjacent to the back waist edge, wherein the second segment includes a visible region and an attachment region, wherein the visible region longitudinally extends beyond the back waist edge such that the visible region is visible from an external vantage point, and wherein the visible region comprises a color, a graphic, a texture feature, or a combination thereof.

4. The disposable absorbent article of claim 3, wherein the attachment region of the second segment comprises a graphic such that the attachment region of the second segment is visible through the topsheet and the backsheet from a vantage point external to the disposable absorbent article.

5. The disposable absorbent article of claim 2, wherein the attachment region of the first segment comprises a color, a graphic, a texture feature, or a combination thereof, such that the attachment region of the first segment is visible through the topsheet and the backsheet from a vantage point external to the disposable absorbent article.

6. The disposable absorbent article of claim 2, wherein the visible region of the first segment comprises an outer surface which is scalloped or serrated.

7. The disposable absorbent article of claim 1, wherein the waist member comprises a first segment including a first waist element attached to one of the pair of front side panels, a second waist element attached to another of the pair of front side panels, and a third waist element attached to a portion of the topsheet, wherein the first waist element, the second waist element, and the third waist element, are disposed on the wearer-facing surface of the disposable absorbent article, and wherein the first waist element is attached to the third waist element in an overlapping manner, and the second waist element is attached to the third waist element in an overlapping manner.

8. A disposable pant for wearing about the lower torso of a wearer, the disposable pant including a chassis which has a topsheet, a backsheet attached to at least a portion of the top sheet, an absorbent core disposed between the topsheet and the backsheet; a front waist region disposed adjacent to a front waist edge, a back waist region disposed adjacent to a back waist edge, and a crotch region disposed between the front waist region and the back waist region; and a first longitudinal edge and a second longitudinal edge, wherein the chassis has a periphery that is defined by the first longitudinal edge and the second longitudinal edge and the front waist edge and the back waist edge, wherein the absorbent core does not extend to the front waist edge and the back waist edge, the disposable pant further comprising:

a pair of front side panels attached to the chassis in the front waist region, a first front side panel extending outward from the first longitudinal edge in the front waist region and a second front side panel extending outward from the second longitudinal edge in the front waist region;

a pair of back side panels attached to the chassis in the back waist region, a first back side panel extending outward from the first longitudinal edge in the back waist region and a second back side panel extending outward from the second longitudinal edge in the back waist region, wherein the pair of front side panels and the pair of back side panels are capable of attaching to each other, thereby forming a waist opening and a pair of leg openings; and a waist member having a first segment attached to the topsheet in the front waist region and to each of the pair of front side panels and a second segment attached to the top sheet in the back waist region and to each of the pair of back side panels, wherein the first segment and the second segment are attached to a wearer-facing surface of the disposable pant and unattached to an outer-facing surface of the disposable pant, wherein the first segment and the second segment extend to the outer side edges of the front side panels and back side panels, wherein the first segment and the second segment can be attached such that the waist member can encircle a waist of a wearer when the disposable pant is donned on the wearer, and wherein the first segment extends outward from the front waist edge, and the second segment extends outward from the back waist edge, such that the waist member extends beyond the periphery of the chassis outward from the front waist edge or the back waist edge, such that at least a region of the first segment and at least a region of the second segment are visible from a vantage point external to the disposable absorbent article, thereby providing the appearance of a finished front waist edge and the appearance of a finished back waist edge.

9. The disposable pant of claim 8, wherein the pair of front side panels and the pair of back side panels are elastically extensible.

10. The disposable pant of claim 8 wherein the first segment and the second segment are elastically extensible, wherein the first segment in a relaxed state forms rugosities in the front waist region of the chassis, and wherein the second segment in a relaxed state forms rugosities in the back waist region.

11. The disposable pant of claim 10, wherein the first segment comprises a visible region and an attachment region, wherein the visible region longitudinally extends beyond the front waist edge such that the visible region is visible from a vantage point external to the disposable absorbent article, and wherein the visible region comprises a color, a graphic, a texture feature, or a combination thereof.

12. The disposable pant of claim 11, wherein the second segment comprises a visible region and an attachment region, wherein the visible region longitudinally extends beyond the back waist edge such that the visible region is visible from a vantage point external to the disposable absorbent article, and wherein the visible region comprises a color, a graphic, a texture feature, or a combination thereof.

13. The disposable pant of claim 12, wherein the attachment region of the second segment comprises a color, a graphic, a texture feature, or a combination thereof such that the attachment region of the second segment is visible through the topsheet and the backsheet from a vantage point external to the disposable absorbent article.

14. The disposable pant of claim 11, wherein the attachment region of the first segment comprises a color, a graphic, a texture feature, or a combination thereof such that the attachment region of the first segment is visible through the topsheet and the backsheet from a vantage point external to the disposable absorbent article.

15. The disposable pant of claim 11, wherein the visible region of the first segment comprises an outer surface which is scalloped or serrated.

16. The disposable pant of claim 8, wherein the first segment comprises a first waist element attached to the first front side panel, a second waist element attached to the second front side panel, and a third waist element attached to a portion of the topsheet, wherein the first waist element, the second waist element, and the third waist element, are disposed on the wearer-facing surface of the disposable pant, and wherein the first waist element is attached to the third waist element in an overlapping manner, and the second waist element is attached to the third waist element in an overlapping manner.

17. The disposable pant of claim 16, wherein the second segment comprises a fourth waist element attached the first back side panel, a fifth waist element attached to the second back side panel, and a sixth waist element attached to a portion of the topsheet, wherein the fourth waist element, fifth waist element, and sixth waist element, are disposed on the wearer-facing surface of the disposable pant, and wherein the fourth waist element is attached to the sixth waist element in an overlapping manner, and the fifth waist element is attached to the sixth waist element in an overlapping manner.

18. The disposable pant of claim 8 further comprising a first edge member and a second edge member, wherein the first edge member is attached to the chassis along the first longitudinal edge, and the second edge member is attached to the chassis along the second longitudinal edge.

19. A disposable pant-like absorbent article for wearing about the lower torso of a wearer, the disposable pant-like absorbent article including a chassis, an outer cover having a front waist region, a back waist region, and a crotch region disposed between the front waist region and the back waist region, a first backsheet layer which defines an outer surface of the disposable pant-like absorbent article, wherein the chassis has a periphery that is defined by longitudinal edges and a front waist edge and a back waist edge, the disposable pant-like absorbent article further comprising:

(a.) a pair of elastically extensible front side panels attached to a portion of the first backsheet layer and disposed on a wearer-facing surface of the disposable pant-like absorbent article;

(b.) a pair of elastically extensible back side panels attached to a portion of the first backsheet layer and disposed on the wearer-facing surface of the disposable pant-like absorbent article;

(c.) an absorbent assembly having a first longitudinal edge and a second longitudinal edge, wherein the absorbent assembly comprises a topsheet, a second backsheet layer associated with the topsheet and an absorbent core disposed between said topsheet and the second backsheet layer, wherein the absorbent core does not extend to the front waist edge and the back waist edge, wherein the second backsheet layer is disposed on the first backsheet layer, wherein the absorbent assembly is attached to the wearer-facing surface of the disposable pant-like absorbent article such that the first and second longitudinal edges are in a spaced apart relationship with each of the front and back side panels, thereby defining a front longitudinally orientated non-elasticized portions and a rear longitudinally orientated non-elasticized portions therebetween;

(d.) a first barrier cuff attached to the first longitudinal edge of the absorbent assembly;

(e.) a second barrier cuff attached to the second longitudinal edge of the absorbent assembly; and (f.) a waist member having a first segment attached to the topsheet in the front waist region and to each of the pair of front side panels and a second segment attached to the topsheet in the back waist region and to each of the pair of back side panels, wherein the first segment and the second segment are attached to the topsheet on a wearer-facing surface of the disposable pant-like absorbent article and unattached to an outer-facing surface of the first backsheet layer, wherein the first segment and the second segment extend to the outer side edges of the front side panels and back side panels, wherein the first segment and the second segment can be attached such that the waist member can encircle a waist of a wearer when the disposable pant-like absorbent article is donned on the wearer, and wherein the first segment extends outward from the front waist edge, and the second segment extends outward from the back waist edge, such that the waist member extends beyond the periphery of the chassis outward from the front waist edge or the back waist edge, such that at least a region of the first segment and at least a region of the second segment are visible from a vantage point external to the disposable pant-like absorbent article, thereby providing the appearance of a finished front waist edge and the appearance of a finished back waist edge.

* * * * *